(12) United States Patent
Fukase

(10) Patent No.: US 11,052,425 B2
(45) Date of Patent: Jul. 6, 2021

(54) ULTRASONIC PROBE WITH HEAT DISSIPATION

(71) Applicant: Konica Minolta Inc., Chiyoda-ku Tokyo (JP)

(72) Inventor: Hirokazu Fukase, Kawasaki Kanagawa (JP)

(73) Assignee: KONICA MINOLTA, INC., Tokyo (JP)

( * ) Notice: Subject to any disclaimer, the term of this patent is extended or adjusted under 35 U.S.C. 154(b) by 617 days.

(21) Appl. No.: 15/948,169

(22) Filed: Apr. 9, 2018

(65) Prior Publication Data

US 2018/0290176 A1 Oct. 11, 2018

(30) Foreign Application Priority Data

Apr. 10, 2017 (JP) .............................. JP2017-077231

(51) Int. Cl.
| | | |
|---|---|---|
| *B06B 1/06* | (2006.01) | |
| *H01L 41/04* | (2006.01) | |
| *G01N 29/32* | (2006.01) | |
| *A61B 8/00* | (2006.01) | |
| *G01N 29/24* | (2006.01) | |
| *G01N 29/22* | (2006.01) | |

(52) U.S. Cl.
CPC .......... *B06B 1/0685* (2013.01); *A61B 8/4444* (2013.01); *B06B 1/067* (2013.01); *G01N 29/223* (2013.01); *G01N 29/2437* (2013.01); *G01N 29/32* (2013.01); *H01L 41/04* (2013.01); *B06B 2201/76* (2013.01); *G01N 2291/02475* (2013.01)

(58) Field of Classification Search
CPC ... B06B 1/0685; B06B 1/067; B06B 2201/76; G01N 29/223; G01N 29/32; G01N 29/2437; G01N 2291/02475; H01L 41/04; A61B 8/4444
See application file for complete search history.

(56) References Cited

U.S. PATENT DOCUMENTS

| | | | | |
|---|---|---|---|---|
| 5,545,942 A | * | 8/1996 | Jaster ...................... | A61B 8/546 174/16.3 |
| 9,307,325 B2 | * | 4/2016 | Kent ....................... | H04R 31/00 |

(Continued)

FOREIGN PATENT DOCUMENTS

| | | |
|---|---|---|
| JP | 2007158468 A | 6/2007 |
| JP | 4408899 B2 | 2/2010 |

(Continued)

OTHER PUBLICATIONS

JPO Notice of Reasons for Refusal for corresponding JP Application No. 2017-077231; dated Jan. 5, 2021.

*Primary Examiner* — Emily P Pham
(74) *Attorney, Agent, or Firm* — Cantor Colburn LLP

(57) ABSTRACT

An ultrasonic probe includes: an acoustic element that generates an ultrasonic wave and detects the ultrasonic wave; a support that supports the acoustic element on a side opposite to a test object side; and a heat dissipation material disposed on a side of the support opposite to the acoustic element, wherein an attenuation/thermal conduction material made of an attenuating material containing a thermally conductive material is disposed in contact with the heat dissipation material.

6 Claims, 5 Drawing Sheets

(56) References Cited

U.S. PATENT DOCUMENTS

| | | | | |
|---|---|---|---|---|
| 2003/0029010 A1* | 2/2003 | Aime | ............... | G10K 11/002 |
| | | | | 29/25.35 |
| 2006/0043839 A1* | 3/2006 | Wildes | ............. | G10K 11/004 |
| | | | | 310/327 |
| 2008/0139945 A1* | 6/2008 | Hu | ................. | G01S 7/52017 |
| | | | | 600/459 |
| 2014/0375171 A1* | 12/2014 | Tai | ................. | B06B 1/0622 |
| | | | | 310/341 |
| 2016/0260885 A1* | 9/2016 | Wang | ............... | H01L 41/04 |
| 2017/0164926 A1* | 6/2017 | Spicci | ............... | A61B 8/546 |

FOREIGN PATENT DOCUMENTS

| | | | |
|---|---|---|---|
| JP | 2013077883 A | 4/2013 | |
| JP | 5828703 B2 | 12/2015 | |

\* cited by examiner

ULTRASONIC PROBE WITH HEAT DISSIPATION

CROSS REFERENCE TO RELATED APPLICATION

The present application claims priority under 35 U.S.C. § 119 to Japanese patent Application No. 2017-077231, filed on Apr. 10, 2017, the entire content of which is incorporated herein by reference.

BACKGROUND

Technological Field

The present invention relates to an ultrasonic probe.

Description of the Related Art

Ultrasonic diagnosis obtains heart beat and fetal movement as an ultrasonic image by a simple operation of applying an ultrasonic probe to a body surface, is very safe, and therefore makes it possible to perform a test repeatedly. An ultrasonic diagnostic apparatus used for performing ultrasonic diagnosis and generating and displaying an ultrasonic image is known.

The ultrasonic diagnostic apparatus includes an ultrasonic probe that transmits an ultrasonic wave to a subject and receives the reflected ultrasonic wave.

A conventional ultrasonic probe includes a case, a piezoelectric element, a back load material that is bonded to a back side of the piezoelectric element (side opposite to a living body as a subject) and attenuates an ultrasonic wave, and a heat transfer member that is bonded to a back side of the back load material and transmits heat generated by the ultrasonic wave to the case (for example, refer to JP 5828703 B2).

During ultrasonic diagnosis, heat generated by the ultrasonic wave is transmitted from the back load material to the case via the heat transfer member, and heat is dissipated.

In addition, another ultrasonic probe includes a piezoelectric element, a back load material that is disposed on a back side of the piezoelectric element (side opposite to a living body) and attenuates an ultrasonic wave, first and second heat dissipation members that are disposed on a back side of the back load material and dissipate heat generated by the ultrasonic wave, a sound absorbing member interposed between the first and second heat dissipation members, and a support member that avoids the sound absorbing member and transfers heat between the first and second heat dissipation members (for example, refer to JP 4408899 B2).

During ultrasonic diagnosis, heat generated by an ultrasonic wave is transmitted from the back load material to the first heat dissipation member, and is further transmitted to the second heat dissipation member via the support member for heat dissipation.

In addition, the sound absorbing member absorbs an ultrasonic wave reflected by the first heat dissipation member to reduce noise.

An ultrasonic probe that performs diagnosis while being in contact with a living body generate heat due to ultrasonic wave propagation loss around a piezoelectric element at the time of generation of the ultrasonic wave. Therefore, a living body contact portion at the time of diagnosis has restriction in a heat generation temperature, and it is effective to suppress a driving voltage in order to satisfy the restriction.

In an ultrasonic probe disclosed in JP 5828703 B2, when a drive voltage is suppressed, sensitivity of the ultrasonic probe is lowered. Therefore, an ultrasonic wave emitted to a side opposite to a living body is attenuated by a back load material, and heat is dissipated by a heat transfer member disposed on a back side of the back load material to lower a heat generation temperature of a living body contact portion.

However, in the ultrasonic probe disclosed in JP 5828703 B2, an ultrasonic wave which cannot be completely attenuated by the back load material is transmitted to the heat transfer member, a natural vibration frequency of the heat transfer member and a higher harmonic component thereof are amplified and input to a piezoelectric element as an unnecessary signal, and noise is generated in an ultrasonic diagnostic image disadvantageously.

In addition, an ultrasonic probe disclosed in JP 4408899 B2 reduces noise by disposing a sound absorbing member between the first and second heat dissipation members on a back side of the back load material. However, the sound absorbing member suppresses heat transfer, and a sufficient heat dissipation effect cannot be obtained disadvantageously.

SUMMARY

An object of the present invention is to provide an ultrasonic probe capable of reducing noise generated by a natural vibration frequency of a member that dissipates heat and a higher harmonic wave thereof without suppressing a heat dissipation effect.

To achieve the abovementioned object, according to an aspect of the present invention, an ultrasonic probe reflecting one aspect of the present invention comprises:

an acoustic element that generates an ultrasonic wave and detects the ultrasonic wave;

a support that supports the acoustic element on a side opposite to a test object side; and a heat dissipation material disposed on a side of the support opposite to the acoustic element, wherein an attenuation/thermal conduction material made of an attenuating material containing a thermally conductive material is disposed in contact with the heat dissipation material.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

First Embodiment

Hereinafter, a first embodiment of the present invention will be described with reference to the drawings. However, various technically preferable limitations for implementing the present invention are given to embodiment described below, but the scope of the invention is not limited to the following embodiment and illustrated examples.

[Ultrasonic Image Diagnostic Apparatus]

Figure 1:
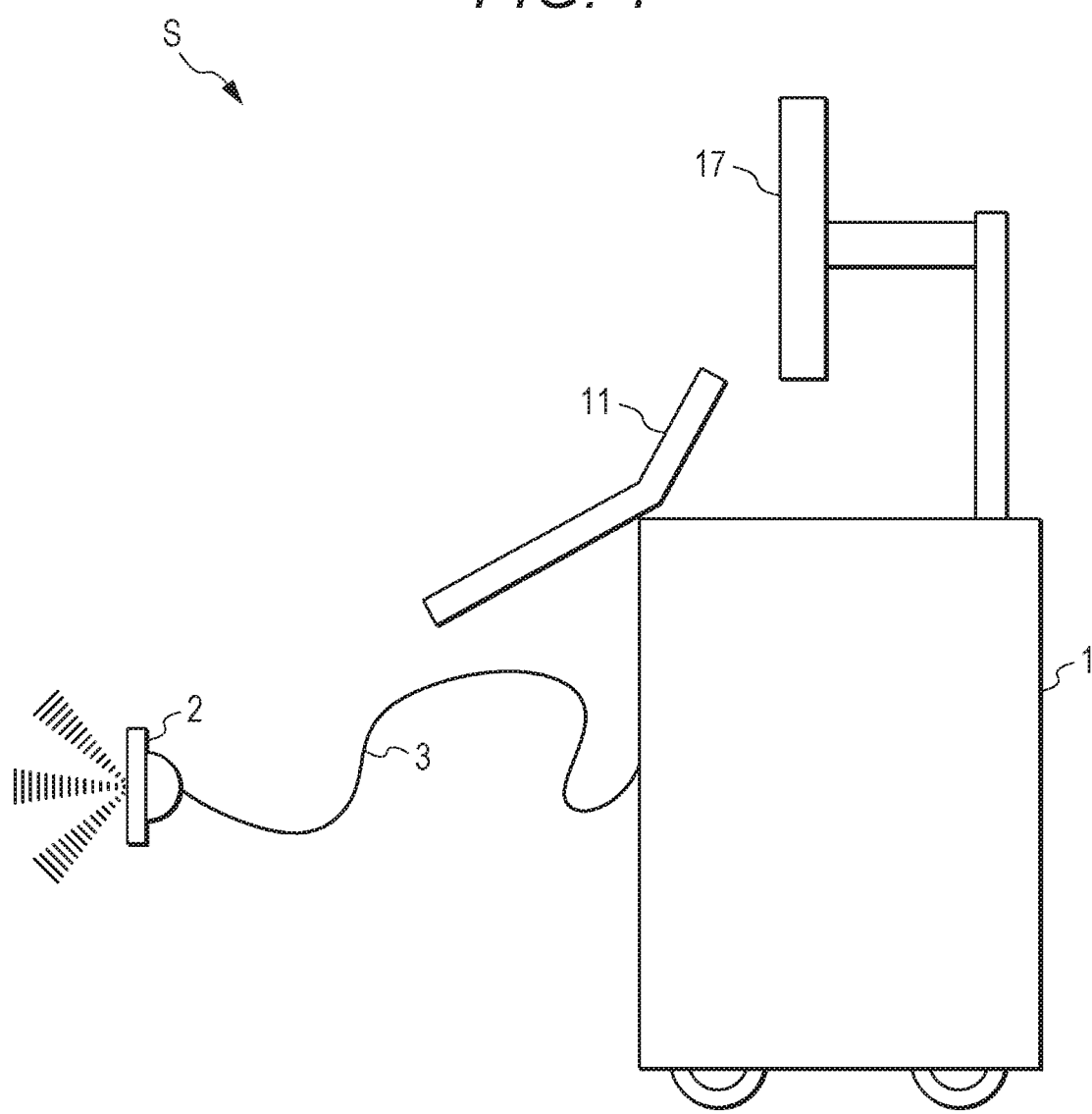
FIG. 1 is an external view of an ultrasonic diagnostic apparatus according to a first embodiment of the present invention.
Figure 2:
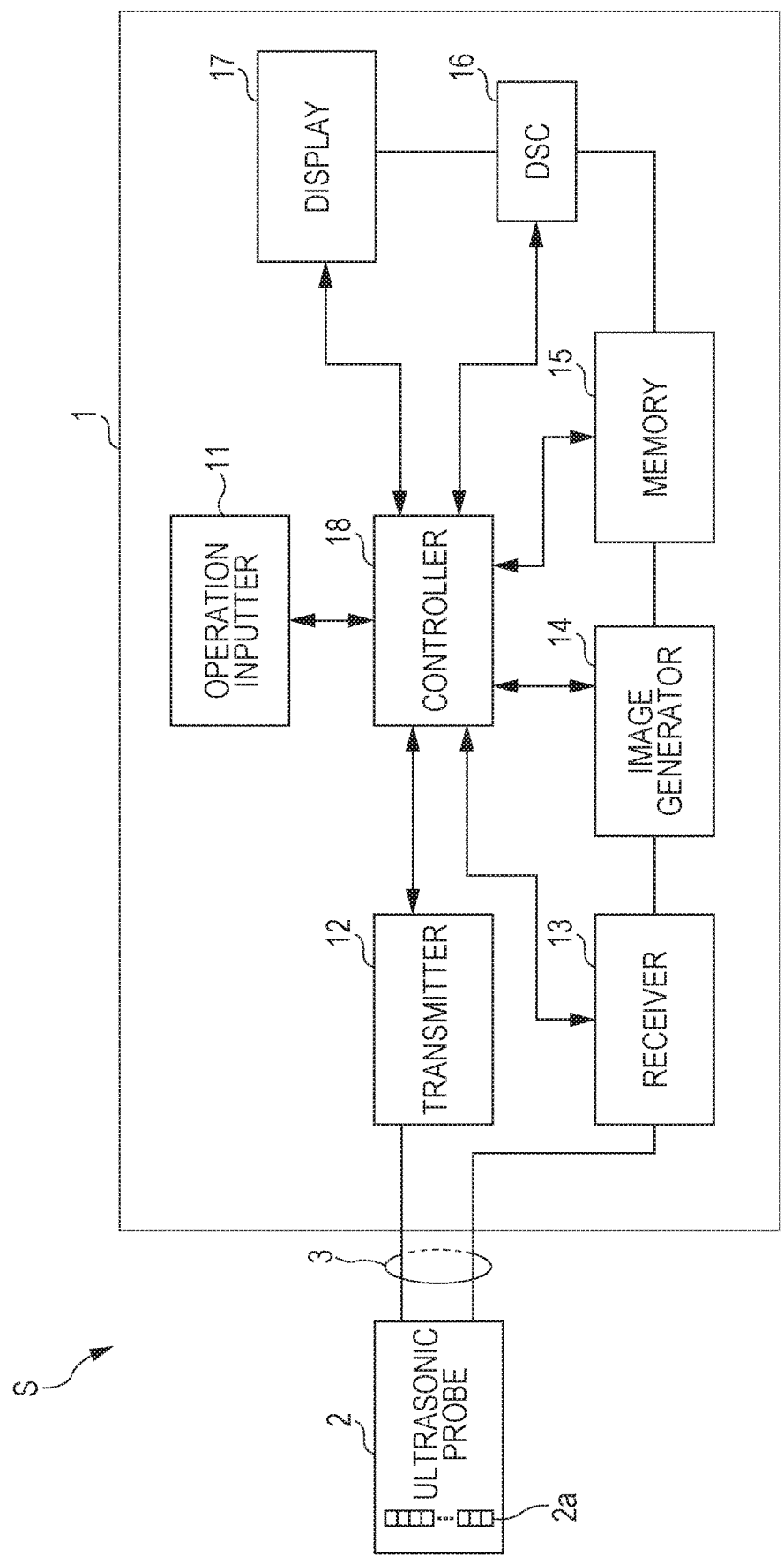
FIG. 2 is a block diagram illustrating a functional configuration of the ultrasonic diagnostic apparatus.

As illustrated in FIG. 1 and FIG. 2, an ultrasonic image diagnostic apparatus S including an ultrasonic probe 2 according to the present embodiment includes an ultrasonic image diagnostic apparatus main body 1 and the ultrasonic probe 2. The ultrasonic probe 2 transmits an ultrasonic wave (transmission ultrasonic wave) to a subject such as a living body (not illustrated) as a test object for the ultrasonic image diagnostic apparatus S, and receives a reflected wave (reflected ultrasonic wave: echo) of the ultrasonic wave reflected by the subject. The ultrasonic image diagnostic apparatus main body 1 is connected to the ultrasonic probe 2 via a cable 3, and transmits a driving signal of an electric signal to the ultrasonic probe 2 to cause the ultrasonic probe 2 to transmit a transmission ultrasonic wave to a subject. In addition, the ultrasonic image diagnostic apparatus main body 1 images an internal state of the subject as an ultrasonic image based on a reception signal as an electric signal generated by the ultrasonic probe 2 in accordance with a reflected ultrasonic wave from an inside of the subject received by the ultrasonic probe 2.

The ultrasonic probe 2 includes, for example, a plurality of transducers 2a arranged in a one-dimensional array in an azimuth direction. In the present embodiment, for example, the ultrasonic probe 2 including 192 transducers 2a is used. Note that the transducers 2a may be arranged in a two-dimensional array. In addition, the number of the transducers 2a can be arbitrarily set. In addition, in the present embodiment, a linear scanning system electronic scanning probe is adopted for the ultrasonic probe 2. However, either the electronic scanning system or a mechanical scanning system may be adopted, and any one of the linear scanning system, a sector scanning system, and a convex scanning system can be adopted.

For example, as illustrated in FIG. 2, the ultrasonic image diagnostic apparatus main body 1 includes an operation inputter 11, a transmitter 12, a receiver 13, an image generator 14, a memory 15, a digital scan converter (DSC) 16, a display 17, and a controller 18.

The operation inputter 11 includes, for example, various switches, a button, a trackball, a mouse, and a keyboard for inputting a command for giving instruction to start diagnosis and data such as personal information on a subject, and outputs an operation signal to the controller 18.

The transmitter 12 is a circuit that supplies a driving signal as an electric signal to the ultrasonic probe 2 via the cable 3 under control of the controller 18 to generate a transmission ultrasonic wave in the ultrasonic probe 2.

The transmitter 12 sequentially switches the plurality of transducers 2a to which driving signals are supplied while shifting the transducers 2a by a predetermined number for each transmission and reception of an ultrasonic wave under control of the controller 18, supplies driving signals to the plurality of transducers 2a which have been selected for output, and thereby performs scanning.

The receiver 13 is a circuit that receives a reception signal of an electric signal from the ultrasonic probe 2 via the cable 3 under control of the controller 18. The receiver 13 adjusts time phases of reception signals from the transducers 2a and adds the obtained results (phase adjustment and addition) to generate sound ray data.

The image generator 14 performs predetermined processing on the sound ray data from the receiver 13 to generate B mode image data. That is, the B mode image data expresses intensity of a reception signal by luminance. The B mode image data generated by the image generator 14 is transmitted to the memory 15.

The memory 15 includes, for example, a semiconductor memory such as a dynamic random access memory (DRAM) and stores the B mode image data transmitted from the image generator 14 in frame units. That is, the memory 15 can store the B mode image data as ultrasonic diagnostic image data constituted in frame units. The ultrasonic diagnostic image data stored in the memory 15 is read under control of the controller 18 and is transmitted to the DSC 16.

The DSC 16 converts the ultrasonic diagnostic image data received from the memory 15 into an image signal according to a television signal scanning system and outputs the image signal to the display 17.

A display device such as a liquid crystal display (LCD), a cathode-ray tube (CRT) display, an organic electronic luminescence (EL) display, an inorganic EL display, or a plasma display can be applied to the display 17. The display 17 displays an ultrasonic diagnostic image on a display screen according to an image signal output from the DSC 16. Note that a printing device such as a printer may be applied instead of the display device.

The controller 18 includes, for example, a central processing unit (CPU), a read only memory (ROM), and a random access memory (RAM), reads various processing programs such as a system program stored in the ROM, develops the programs in the RAM, and centrally controls operation of each part of the ultrasonic image diagnostic apparatus S according to a developed program.

Specifically, the controller 18 controls the transmitter 12 to cause the ultrasonic probe 2 to generate a transmission ultrasonic wave, and controls the receiver 13 to cause the receiver 13 to receive a reception signal of a reflected ultrasonic wave from the ultrasonic probe 2 and to generate sound ray data.

Furthermore, the controller 18 controls the image generator 14 to cause the image generator 14 to generate B mode image data, stores the B mode image data in the memory 15 as ultrasonic diagnostic image data, and controls the DSC 16 to cause the display 17 to display the ultrasonic diagnostic image data.

[Ultrasonic Probe]

Next, the ultrasonic probe 2 according to the present embodiment will be described with reference to FIG. 3.

Figure 3:
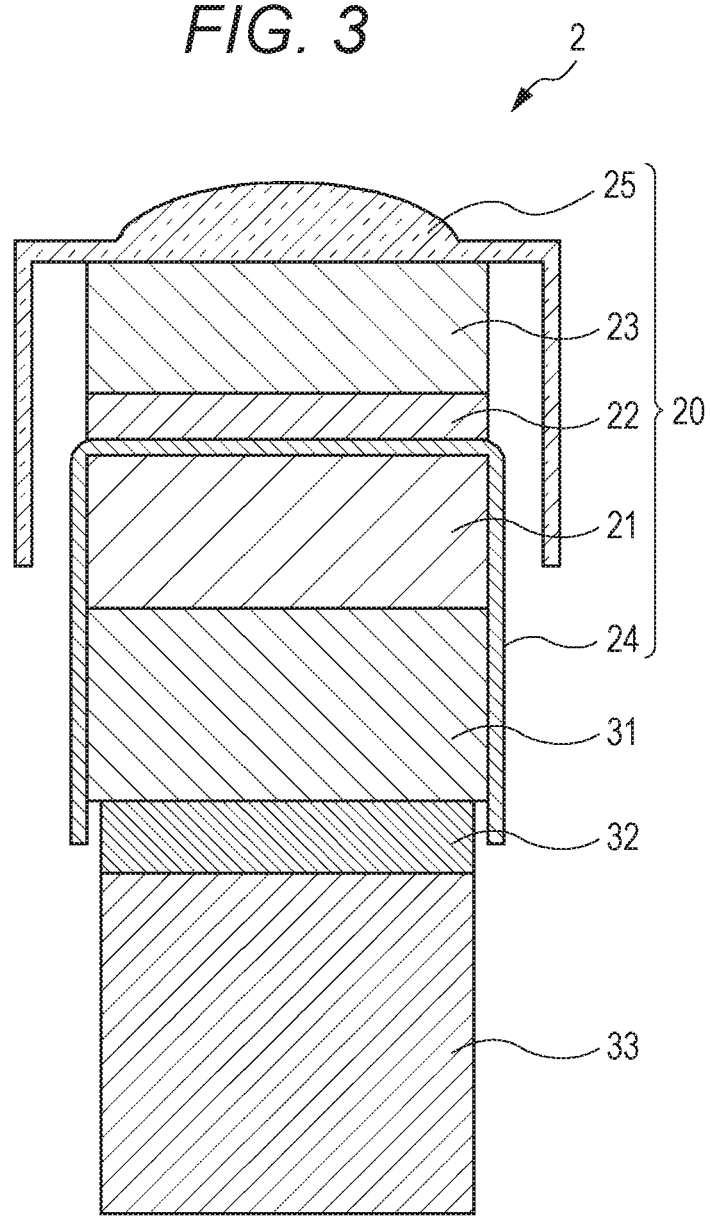
FIG. 3 is a cross-sectional view illustrating an internal configuration of an ultrasonic probe.
Figure 4:
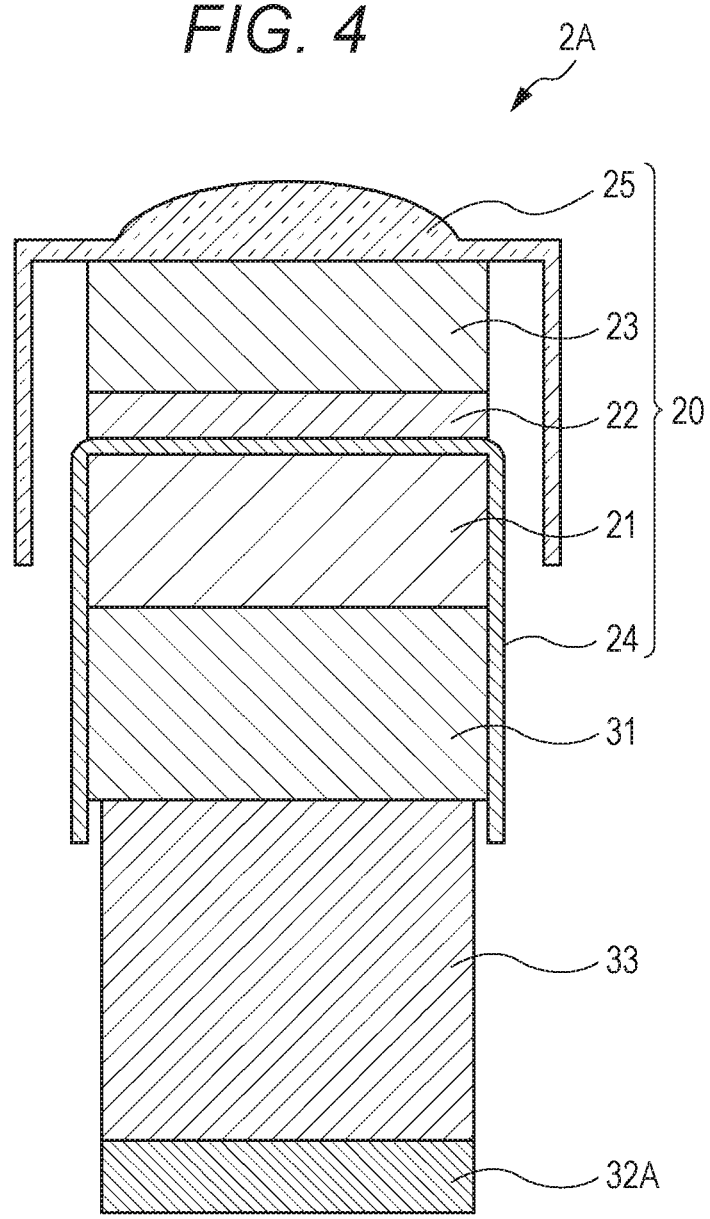
FIG. 4 is a cross-sectional view illustrating an internal configuration of an ultrasonic probe according to a second embodiment of the present invention.
Figure 5:
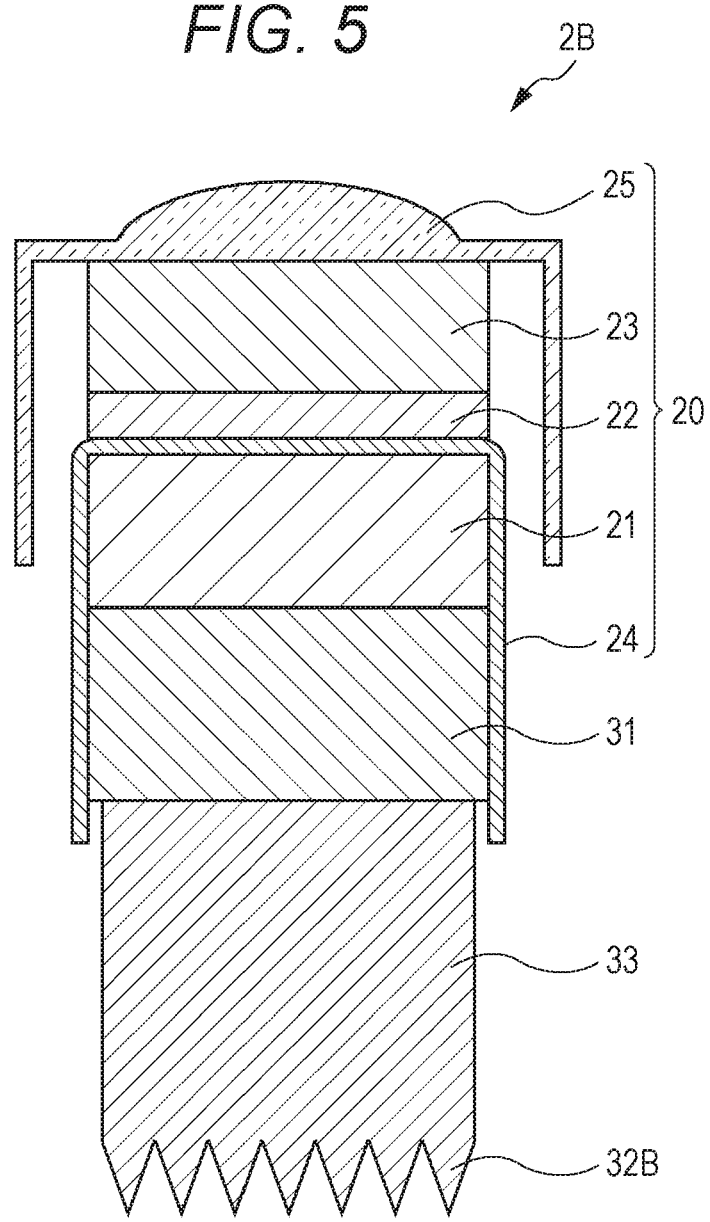
FIG. 5 is a cross-sectional view illustrating an internal configuration of an ultrasonic probe according to a third embodiment of the present invention.

In FIG. 3, the upper side indicates a subject side as a test object, and the lower side indicates a side opposite to the subject (side away from the subject). In the following description, the subject side is referred to as "front side", and a side opposite to the subject (side away from the subject) is referred to as "rear side".

For example, in the ultrasonic probe 2, an acoustic element 20, a reinforcing material 31 as a support body, an attenuation/thermal conduction material 32, and a heat dissipation material 33 are arranged toward the rear side in order from the front side, and a casing (not illustrated) houses and supports these components (excluding an acoustic lens 25 described later).

[Acoustic Element]

In the acoustic element 20, the acoustic lens 25, an acoustic matching layer 23, a piezoelectric element 22, an FPC 24, and a back load material 21 are arranged toward the rear side in order from the front side.

Note that the acoustic lens 25 is brought into contact with a subject, and therefore is held while at least a front surface thereof is exposed from the above-described casing.

[Acoustic Element: Piezoelectric Element]

The piezoelectric element 22 is an element (piezoelectric element) including an electrode and a piezoelectric material, capable of converting an electric signal into mechanical vibration and mechanical vibration into an electric signal, and capable of transmitting and receiving an ultrasonic wave.

The piezoelectric material contains a piezoelectric substance capable of converting an electric signal into a mechanical vibration and a mechanical vibration into an electric signal. Examples of the piezoelectric substance include lead zirconate titanate (PZT)-based ceramics, piezoelectric ceramics such as lead titanate and lead metaniobate, a piezoelectric single crystal made of lithium niobate or a solid solution-based single crystal such as lead zinc niobate and lead titanate or lead magnesium niobate and lead titanate, quartz crystal, Rochelle salt, and an organic polymer piezoelectric material including a PVDF copolymer such as polyvinylidene fluoride-triethylene fluoride (P(VDF-TrFE)) which is a copolymer of polyvinylidene fluoride (PVDF) or VDF and, for example, triethylene fluoride (TrFE), polyvinylidene cyanide (PVDCN) which is a polymer of vinylidene cyanide (VDCN), a vinylidene cyanide-based copolymer, an odd nylon such as nylon 9 or nylon 11, an aromatic nylon, an alicyclic nylon, polylactic acid, a polyhydroxy carboxylic acid such as polyhydroxy butyrate, a cellulose-based derivative, and polyurea.

The thickness of the piezoelectric material is, for example, in a range of 100 to 500 μm. The piezoelectric material is used as the transducers 2a while electrodes are attached to both surfaces thereof.

Examples of a material used for an electrode attached to the piezoelectric material include gold (Au), platinum (Pt), silver (Ag), palladium (Pd), copper (Cu), aluminum (Al), nickel (Ni), and tin (Sn).

In the piezoelectric element 22, an electrode is in contact with a flexible printed circuit (FPC) 24, and the FPC 24 is electrically connected to the cable 3. Therefore, a driving signal output from the ultrasonic image diagnostic apparatus main body 1 is input to the piezoelectric element 22 via the FPC 24, and a reception signal generated by the piezoelectric element 22 is output to the ultrasonic image diagnostic apparatus main body 1.

[Acoustic Element: Back Load Material]

The back load material 21 is disposed on a rear side with respect to the piezoelectric element 22 in a lamination direction of members constituting the ultrasonic probe.

The back load material 21 is made of a material having a lower acoustic impedance than the piezoelectric element 22, and is an ultrasonic wave absorber capable of absorbing an unnecessary ultrasonic wave. That is, the back load material 21 absorbs an ultrasonic wave generated from a rear end of the piezoelectric element 22.

Examples of a material constituting the back load material 21 include a natural rubber, a ferrite rubber, an epoxy resin, a rubber-based composite material or an epoxy resin composite material obtained by adding a powder such as tungsten oxide, titanium oxide, or ferrite, or a micro balloon to these materials and press-molding the resulting mixture, vinyl chloride, polyvinyl butyral (PVB), an ABS resin, polyurethane (PUR), polyvinyl alcohol (PVAL), polyethylene (PE), polypropylene (PP), polyacetal (POM), polyethylene terephthalate (PETP), a fluorocarbon resin (PTFE), and a thermoplastic resin such as polyethylene glycol or a polyethylene terephthalate-polyethylene glycol copolymer.

A preferable shape of the back load material 21 can be appropriately selected according to the shape of the piezoelectric element 22 or a probe head including the piezoelectric element 22.

[Acoustic Element: Acoustic Matching Layer]

The acoustic matching layer 23 matches an acoustic impedance between the piezoelectric element 22 and the acoustic lens 25 and suppresses reflection at an interface among the piezoelectric element 22, the acoustic matching layer 23, and the acoustic lens 25. The acoustic matching layer 23 is attached to a front end surface of the piezoelectric element 22.

The acoustic matching layer 23 may be constituted by a single layer or a plurality of layers, but is preferably constituted by two or more layers. The thickness of each layer of the acoustic matching layer 23 needs to be set to $\lambda/4$ if $\lambda$ represents a wavelength of an ultrasonic wave. If this condition is not satisfied, a plurality of unnecessary spuriouses appear at a frequency point different from an original resonance frequency, and fundamental acoustic characteristics largely fluctuate. As a result, reverberation time increases, and sensitivity or S/N decreases due to waveform distortion of a reflected echo. This is not preferable.

An acoustic impedance of the acoustic matching layer 23 is set so as to gradually decrease from a rearmost layer to a foremost layer and such that an acoustic impedance of the rearmost layer is less than an acoustic impedance of the piezoelectric element 22. In order to match the acoustic impedance of the acoustic matching layer 23 with an acoustic impedance of the acoustic lens 25 described later, a difference between the acoustic impedance of the foremost layer and the acoustic impedance of the acoustic lens 25 is preferably made smaller (the acoustic impedance of the foremost layer and the acoustic impedance of the acoustic lens 25 may be the same as each other).

The thickness of each of a plurality of layers constituting the acoustic matching layer 23 may be less than $1/4\lambda$ in units of wavelength (for example, $\lambda$) corresponding to an acoustic velocity determined by the composition of each layer and a center frequency of an ultrasonic wave transmitted from the piezoelectric element 22. This makes it possible to reduce attenuation by the acoustic matching layer 23 on a low frequency side with respect to the center frequency of an ultrasonic wave.

Specific examples of a material used for the acoustic matching layer 23 include aluminum, an aluminum alloy (for example, an Al—Mg alloy), a magnesium alloy, a Macor glass, glass, a fused quartz, copper graphite, polyethylene (PE), polypropylene (PP), polycarbonate (PC), an ABC resin, an ABS resin, an AAS resin, an AES resin, a nylon (PA6 or PA6-6), polyphenylene oxide (PPO), polyphenylene sulfide (PPS) (may include glass fiber), polyphenylene ether (PPE), polyether ether ketone (PEEK), polyamide imide (PAI), polyethylene terephthalate (PETP), an epoxy resin, and a urethane resin. Preferably, it is possible to apply a material obtained by adding tungsten, zinc white, titanium oxide, silica, alumina, red iron oxide, ferrite, tungsten oxide, yttrium oxide, barium sulfate, molybdenum, or the like as a filler to a thermosetting resin such as an epoxy resin and molding the resulting mixture. Here, by changing the type, amount, distribution, and the like of a filler among layers, even in the same type of resin, the acoustic impedance can be different among layers.

[Acoustic Element: Acoustic Lens]

The acoustic lens 25 is disposed in order to converge an ultrasonic beam by utilizing refraction and to improve resolution. That is, the acoustic lens 25 is disposed on a side of the ultrasonic probe 2 in contact with a subject, and makes an ultrasonic wave generated by the piezoelectric element 22 efficiently enter the subject. The acoustic lens 25 is a portion in contact with a subject, has a convex or concave lens shape according to an internal sound speed, and converges an ultrasonic wave that enters the subject in a thickness direction perpendicular to an imaging cross section (elevation direction).

An acoustic impedance of the acoustic lens 25 is appropriately set such that attenuation and reflection of an ultrasonic wave between the acoustic lens 25 and a subject are smaller than those in an acoustic impedance of the subject. Here, the subject is a human body or the like. Therefore, in general, the acoustic impedance of the acoustic lens 25 is set so as to be extremely lower than that of a hard substance such as the piezoelectric element 22. Therefore, the acoustic lens 25 is made of a material (for example, a soft polymer material or the like) corresponding to a set acoustic impedance.

Examples of a material constituting the acoustic lens 25 include a conventionally known homopolymer such as a silicone-based rubber, a butadiene-based rubber, a polyurethane rubber, or an epichlorohydrin rubber, and a copolymer rubber such as an ethylene-propylene copolymer rubber obtained by copolymerizing ethylene and propylene. Among these materials, a silicone-based rubber and a butadiene-based rubber are preferably used.

[Reinforcing Material]

The reinforcing material 31 is fixed to a casing, supports the acoustic element 20 and the heat dissipation material 33, and transfers heat generated by the acoustic element 20 to the heat dissipation material 33.

Therefore, the acoustic element 20 is disposed behind the back load material 21. A front end surface of the reinforcing material 31 is in close contact with a rear end surface of the back load material 21 by screwing or bonding. In a case where these surfaces are bonded to each other, an adhesive having a high thermal conductivity may be used. In addition, a resin-based adhesive such as an epoxy adhesive may be used so as to form an extremely thin adhesive layer.

Specifically, as a material used for the reinforcing material 31, it is desirable to use a metal such as copper or aluminum, a resin having a high thermal conductivity, or the like.

[Heat Dissipation Material]

The heat dissipation material 33 is connected to a rear end of the reinforcing material 31 via the attenuation/thermal conduction material 32, and is supported by the reinforcing material 31.

The heat dissipation material 33 is elongated in a front-rear direction and has a plate-shaped rear end side. The heat dissipation material 33 is supported only at a front end, and a rear end and a surrounding surface thereof are not supported by a casing. Therefore, the rear end side of the heat dissipation material 33 extends rearward in a state of a free end.

As a material constituting the heat dissipation material 33, a material having a high thermal conductivity, for example, a metal such as copper or aluminum, or carbon graphite is preferable.

[Attenuation/Thermal Conduction Material]

The attenuation/thermal conduction material 32 is disposed between the reinforcing material 31 and the heat dissipation material 33, satisfactorily transfers heat from the reinforcing material 31 to the heat dissipation material 33, and attenuates ultrasonic vibration from the acoustic element 20 side to suppress transfer of an ultrasonic wave to the heat dissipation material.

A rear end surface of the reinforcing material 31, a front end surface of the attenuation/thermal conduction material 32, a rear end surface of the attenuation/thermal conduction material 32, and a front end surface of the heat dissipation material 33 are all smooth. The rear end surface of the reinforcing material 31 and the front end surface of the attenuation/thermal conduction material 32 are connected to each other while being in close contact with each other. The rear end surface of the attenuation/thermal conduction material 32 and the front end surface of the heat dissipation material 33 are connected to each other while being in close contact with each other. As a result, the reinforcing material 31 and the heat dissipation material 33 do not come into direct contact with each other. The reinforcing material 31, the attenuation/thermal conduction material 32, and the heat dissipation material 33 are connected to one another by screwing, bonding, or the like, and an adhesive having a high thermal conductivity is used in a case of bonding.

As a material constituting the attenuation/thermal conduction material 32, an attenuating material containing a thermally conductive material, for example, a resin such as silicone or epoxy having a higher thermal conductivity by containing a metal filler as a thermally conductive material is preferable.

The thermal conductivity of the attenuation/thermal conduction material 32 is 0.5 W/(m K) or more. An upper limit thereof is desirably about the same as that of the heat dissipation material 33, and may be higher if possible.

An ultrasonic wave attenuation ratio of the attenuation/thermal conduction material 32 is 3 dB/mm at 5 MHz or more. An upper limit thereof is desirably about the same as that of the back load material 21, and may be higher if possible.

The thermal conductivity and the ultrasonic wave attenuation ratio of the attenuation/thermal conduction material 32 can be adjusted by the content of a metal filler with respect to a main material such as silicone or epoxy.

[Operation of Ultrasonic Probe]

In the ultrasonic probe 2 having the above configuration, when a driving signal as an electric signal is supplied from the transmitter 12 of the ultrasonic image diagnostic apparatus S via the cable 3, a voltage is applied to the piezoelectric element 22 of the acoustic element 20, and is converted into an ultrasonic wave. The ultrasonic wave is transmitted to a subject via the acoustic matching layer 23 and the acoustic lens 25. Then, a reflected ultrasonic wave generated by the subject is received by the piezoelectric element 22, and is converted into a reception signal. The reception signal is transmitted to the receiver 13 of the ultrasonic image diagnostic apparatus S via the cable 3.

Meanwhile, in the ultrasonic probe 2, when an ultrasonic wave is transmitted from the piezoelectric element 22 toward a subject, the ultrasonic wave is also emitted to a back side of the piezoelectric element 22. Many of the emitted ultrasonic waves are attenuated by the back load material 21, but a part thereof is transmitted to the reinforcing material 31.

Then, the ultrasonic wave transmitted to the reinforcing material 31 is directed to the heat dissipation material 33. However, the attenuation/thermal conduction material 32 is interposed between the reinforcing material 31 and the heat dissipation material 33. Therefore, many of the ultrasonic waves are attenuated, and the amount of transfer thereof to the heat dissipation material 33 is effectively reduced.

When the piezoelectric element 22 transmits an ultrasonic wave, the acoustic element 20 generates heat. Heat generated by the acoustic element 20 is directed to the heat dissipation material 33 via the reinforcing material 31 and the attenuation/thermal conduction material 32, and is dissipated from a surface of the heat dissipation material 33. At this time, the attenuation/thermal conduction material 32 is present in a heat transfer path. However, the attenuation/thermal conduction material 32 contains a thermally conductive material. Therefore, heat is transferred satisfactorily, and heat is dissipated effectively.

[Technical Effect in First Embodiment]

In the ultrasonic probe 2, the attenuation/thermal conduction material 32 containing a thermally conductive material is disposed in contact with the heat dissipation material 33, and therefore the attenuation/thermal conduction material 32 does not hinder transfer of heat generated by the acoustic element 20 to the heat dissipation material 33, and heat can be dissipated effectively.

In addition, many of ultrasonic waves directed from the reinforcing material 31 to the heat dissipation material 33 are attenuated by the attenuation/thermal conduction material 32, and transfer of the ultrasonic waves to the heat dissipation material 33 is suppressed. Therefore, it is possible to effectively reduce noise generated by a natural vibration frequency of the heat dissipation material 33 and a higher harmonic wave thereof.

Particularly, the attenuation/thermal conduction material 32 is disposed on the acoustic element 20 side of the heat dissipation material 33. Therefore, heat generated by the acoustic element 20 can be satisfactorily transferred to the heat dissipation material 33, and heat can be dissipated effectively.

Furthermore, an ultrasonic wave directed from the reinforcing material 31 to the heat dissipation material 33 is attenuated by the attenuation/thermal conduction material 32. Therefore, it is possible to more effectively reduce noise generated by a natural vibration frequency of the heat dissipation material 33 and a higher harmonic wave thereof.

Second Embodiment

Hereinafter, an ultrasonic probe 2A according to a second embodiment of the present invention will be described with reference to the drawings. However, various technically preferable limitations for implementing the present invention are given to embodiment described below, but the scope of the invention is not limited to the following embodiment and illustrated examples.

Incidentally, for the ultrasonic probe 2A, the same components as those of the above-described ultrasonic probe 2 are denoted by the same reference numerals, and redundant description thereof is omitted.

In the ultrasonic probe 2A, instead of the attenuation/thermal conduction material 32, an attenuation/thermal conduction material 32A is disposed not between a reinforcing material 31 and a heat dissipation material 33 but on a rear end surface of the heat dissipation material 33.

The attenuation/thermal conduction material 32A is made of the same material as the above-described attenuation/thermal conduction material 32 of the ultrasonic probe 2 and has the same shape as a rear end surface of the heat dissipation material 33.

In the ultrasonic probe 2A, the attenuation/thermal conduction material 32A is disposed at a rear end of the heat dissipation material 33. Therefore, reflection of an ultrasonic wave transmitted from the reinforcing material 31 to the heat dissipation material 33 on a rear end surface of the heat dissipation material 33 is suppressed, and it is possible to effectively reduce noise generated by a natural vibration frequency of the heat dissipation material 33 and a higher harmonic wave thereof.

In addition, by disposition of the attenuation/thermal conduction material 32A made of a material different from the heat dissipation material 33 at a rear end of the heat dissipation material 33, a vibration system that determines a natural vibration frequency is different from the case where only the heat dissipation material 33 is disposed, and it is possible to effectively reduce noise generated by a natural vibration frequency of the heat dissipation material 33 and a higher harmonic wave thereof.

Furthermore, no attenuation/thermal conduction material is interposed between the reinforcing material 31 and the heat dissipation material 33, and the reinforcing material 31 and the heat dissipation material 33 are directly connected to each other. Therefore, heat generated by an acoustic element 20 is satisfactorily transferred to the heat dissipation material 33, and heat can be dissipated effectively.

In addition, the attenuation/thermal conduction material 32A includes a thermally conductive material and is made of a material having a high thermal conductivity. Therefore, heat is propagated from the heat dissipation material 33, and the attenuation/thermal conduction material 32A itself also dissipates heat. Therefore, heat can be dissipated more effectively.

Third Embodiment

Hereinafter, an ultrasonic probe 2B according to a third embodiment of the present invention will be described with reference to the drawings. However, various technically preferable limitations for implementing the present invention are given to embodiment described below, but the scope of the invention is not limited to the following embodiment and illustrated examples.

Incidentally, for the ultrasonic probe 2B, the same components as those of the above-described ultrasonic probe 2 are denoted by the same reference numerals, and redundant description thereof is omitted.

In the ultrasonic probe 2B, instead of the attenuation/thermal conduction material 32, an attenuator 32B having a multifaceted scattering structure is formed at a rear end of a heat dissipation material 33.

The attenuator 32B has a sawtooth shape when viewed from a direction perpendicular to a front-rear direction. As a result, a rear end of the heat dissipation material 33 is not a smooth surface perpendicular to the front-rear direction, but includes many surfaces inclined in the front-rear direction and each having a small area.

In the ultrasonic probe 2B, the attenuator 32B having a multifaceted scattering structure is disposed at a rear end of the heat dissipation material 33. Therefore, an ultrasonic wave transmitted from a reinforcing material 31 to the heat dissipation material 33 is scattered by many inclined surfaces formed at a rear end of the heat dissipation material 33. It is possible to reduce intensity of an ultrasonic wave reflected toward an acoustic element 20 side, and to effectively reduce noise generated by a natural vibration frequency of the heat dissipation material 33 and a higher harmonic wave thereof.

Furthermore, no attenuation/thermal conduction material is interposed between the reinforcing material 31 and the heat dissipation material 33, and the reinforcing material 31 and the heat dissipation material 33 are directly connected to each other. Therefore, heat generated by the acoustic element 20 is satisfactorily transferred to the heat dissipation material 33, and heat can be dissipated effectively.

In addition, the attenuator 32B includes many inclined surfaces. Therefore, a surface area can be increased, and heat can be dissipated more effectively.

Particularly, because of a sawtooth-shaped structure of the attenuator 32B, many portions extending in a sharp shape are generated. Therefore, heat can be dissipated more effectively also due to this shape.

Note that the above-described attenuation/thermal conduction material 32 may be further disposed at an end of the heat dissipation material 33 on the acoustic element 20 side.

Although embodiments of the present invention have been described and illustrated in detail, the disclosed embodiments are made for purposes of illustration and example only and not limitation. The scope of the present invention should be interpreted by terms of the appended claims.

What is claimed is:

1. An ultrasonic probe comprising:
an acoustic element that generates an ultrasonic wave and detects the ultrasonic wave, the acoustic element including a lens and a flexible printed circuit, the lens disposed at a first side of the flexible printed circuit;
a support that supports the acoustic element on an acoustic element side opposite to a test object side, the support disposed at a second side of the flexible printed circuit opposite the first side; and
a heat dissipation material disposed on a side of the support opposite to the acoustic element, wherein
an attenuation/thermal conduction material made of an attenuating material containing a thermally conductive material is disposed in contact with the heat dissipation material.

2. The ultrasonic probe according to claim 1, wherein the attenuation/thermal conduction material is disposed at an end of the heat dissipation material on the acoustic element side.

3. The ultrasonic probe according to claim 1, wherein the attenuation/thermal conduction material is disposed at an end of the heat dissipation material on a side opposite to the acoustic element side.

4. The ultrasonic probe according to claim 3, wherein the attenuation/thermal conduction material is made of a material different from the heat dissipation material.

5. An ultrasonic probe comprising:
an acoustic element that generates an ultrasonic wave and detects the ultrasonic wave, the acoustic element including a lens and a flexible printed circuit, the lens disposed at a first side of the flexible printed circuit;
a support that supports the acoustic element on a side opposite to a test object side, the support disposed at a second side of the flexible printed circuit opposite the first side; and
a heat dissipation material disposed on a side of the support opposite to the acoustic element, wherein
an attenuator having a multifaceted scattering structure is formed at an end of the heat dissipation material on a side opposite to the acoustic element side.

6. The ultrasonic probe according to claim 5, wherein the multifaceted scattering structure is a sawtooth-shaped structure.

* * * * *